United States Patent [19]

Marshall

[11] Patent Number: 5,256,684
[45] Date of Patent: Oct. 26, 1993

[54] METHODS AND COMPOSITIONS FOR THE TREATMENT OF GASTROINTESTINAL DISORDERS

[75] Inventor: Barry J. Marshall, Charlottesville, Va.

[73] Assignee: The Procter & Gamble Company, Cincinnati, Ohio

[21] Appl. No.: 737,573

[22] Filed: Jul. 26, 1991

Related U.S. Application Data

[63] Continuation of Ser. No. 62,271, Jun. 15, 1987, abandoned, which is a continuation of Ser. No. 744,841, Jun. 13, 1985, abandoned.

[51] Int. Cl.$^5$ ............... A61K 31/415; A61K 33/24; A61K 31/70; A61K 31/65; A61K 31/61; A61K 31/43; A61K 31/545; A61K 31/29
[52] U.S. Cl. ................ 514/398; 424/650; 424/653; 514/29; 514/37; 514/39; 514/41; 514/154; 514/163; 514/192; 514/198; 514/199; 514/200; 514/390; 514/503; 514/926; 514/927
[58] Field of Search ............ 514/503, 29, 37, 39, 514/41, 154, 163, 192, 198, 199, 200, 390, 398, 926, 927; 424/650, 653

[56] References Cited

U.S. PATENT DOCUMENTS

| | | | |
|---|---|---|---|
| 3,247,051 | 4/1966 | Leebrick | 167/22 |
| 4,016,268 | 4/1977 | Goldenberg et al. | 424/231 |
| 4,153,685 | 5/1979 | Serfontein | 424/94 |

FOREIGN PATENT DOCUMENTS

| | | |
|---|---|---|
| 5877M | 4/1968 | France . |
| 772567 | 4/1957 | United Kingdom . |
| 1478742 | 7/1977 | United Kingdom . |

OTHER PUBLICATIONS

McGraw-Hill, "Dictionary of Scientific and Technical Terms, Second Ed." (1978), p. 665.
Stedman's Medical Dictionary, 24th Ed. (1982) p. 577.
Heraud et al., "Therapeutic trial of an association of an insoluble bismuth salt and a Karaya gum in gastro-intestinal pathology", Lille Medical, 3rd Series vol. XIV, No. 6, supplement, pp. 677-679 (1969).
Abstract: "Histological Improvement of Active Chronic Gastritis in Patients Treated with De-Nol", presented at a meeting of the Gastroenterological Society of Australia, Mar. 11-14, 1984, Melbourne, Australia.
M. B. Skirrow, "Report on the Session" in Campylobacter 11, Proceedings of the Second International Workshop on Campylobacter Infections (London, 1983; Public Health Laboratory Service; Pearson, Skirrow et al., editors), pp. 5-10.
Marshall and Warren, "Spiral bacteria in the human stomach: a common finding in patients with gastritis and duodenal ulcer" in: Campylobacter II, Proceedings of the Second International Workhip on Campylobacter Infections (London, 1983; Public Health Laboratory Service; Pearson, Skirrow et al., editors), pp. 11-12.
Gisselbrecht et al., "Treatment of constipation and colitis by the association of bismuth subnitrate and Karaya gum", Lyon Med., 223(18), pp. 951-958 (1970).
Navarranne, "Treatment of spasmodic and psychosomatic colopathies by a cicatrisant, antiseptic and anxiolytic medication combination", Therapie, XXII, pp. 419-426 (1967).

(List continued on next page.)

Primary Examiner—Frederick E. Waddell
Assistant Examiner—Raymond J. Henley, III
Attorney, Agent, or Firm—J. D. Schaeffer; D. C. Mohl; K. M. Harleston

[57] ABSTRACT

Methods, for the treatment of humans and lower animal subjects having a gastrointestinal disorder, comprising administering bismuth and administering an antimicrobial. From about 50 to about 5000 milligrams of bismuth are administered, per day, for from 3 to 56 days. A safe and effective amount of antimicrobial is administered for from 1 to 21 days. Preferred processes also include a step for performing a diagnostic test on the subject for detection of a campylobacter-like organism infection of the subject. The invention also provides compositions containing a safe and effective amount of bismuth and a safe and effective amount of antimicrobial.

49 Claims, No Drawings

OTHER PUBLICATIONS

Colson, "The treatment of chronic colitis and colpathies by a new association of bismuth, mucilage, oxyquinoline and meprobamate", *Revue des corps de sante des Armees*, 7(2), pp. 319-334 (1966).

A. Freedberg, et al., "The Presence of Spirochetes in Human Gastric Mucosa", 7 *American Journal of Digestive Diseases* 443-445 (1940).

M. Goldenberg, et al., "Protective Effects of Pepto-Bismol Liquid on the Gastric Mucosa of Rats", 69 *Gastroenterology* 636-640 (1975).

M. Steinhoff, et al., "Bismuth Subsalicylate Therapy of Viral Gastroenteritis", 78 *Gastroenterology* 1495-1499 (1980).

M. Blaser, et al., "Campylobacter Enteritis", 305 *New England Journal of Medicine* 1444-1452 (1981).

J. Koo, et al., "Selective Coating of Gastric Ulcer by Tripotassium Dicitrato Bismuthate in the Rat", 82 *Gastroenterology* 864-870 (1982).

M. Gregory, "The Effect of Tri-potassium Di-citrato Bismuthate on the Duodenal Mucosa During Ulceration" 62 *S.A. Medical Journal* 52-55 (1982).

J. Warren, "Unidentified Curved Bacilli on Gastric Epithelium in Active Chronic Gastitis" 1 *Lancet* 1273 (1983).

B. Marshall, "Unidentified Curved Bacilli on Gastric Epithelium in Active Chronic Gastitis" 1 *Lancet* 1273-1275 (1983).

Z. Zheng, et al., "A Double-blind Short-term Clinical Trial of the Effect of Furazolidone in Peptic Ulcer", 23 *Chinese J. of Int. Medicine* 195-197 (1984).

C. McNulty, et al., "Spiral Bacteria of the Gastric Antrum" 1 *Lancet* 1068 (1984).

B. Marshall, et al., "Unidentified Curved Bacilli in the Stomach of Patients with Gastritis and Peptic Ulceration" 1 *Lancet* 1311-1315 (1984).

M. Langenberg, et al., "Campylobacter-like Organisms in the Stomach of Patients and Healthy Individuals" 1 *Lancet* 1348 (1984).

R. Burnett, et al., "Campylobacter-like Organisms in the Stomach of Patients and Healthy Individuals" 1 *Lancet* 1349 (1984).

B. Marshall, et al., "Pyloric Campylobacter Serology" 2 *Lancet* 281 (1984).

A. McLean, et al., "Microbes, Peptic Ulcer and Relapse Rates with Different Drugs", 2 *Lancet* 525-526 (1984).

B. Marshall, et al., "Pyloric Campylobacter Infection and Gastroduodenal Disease" 142 *Medical Journal of Australia* 439-444 (1985).

Z. Zheng, et al., "Bouble-blind Short-term Trial of Furazolidone in Peptic Ulcer" 1 *Lancet* 1048-1049 (1985).

C. McNulty, et al., "Rapid Diagnosis of Campylobacter-Associated Gastrtis" 1 *Lancet* 1443-1444 (1985).

K. I. Shirokova, et al., "The Use of Metronidazole in Treatment of Patients with Ulcerative Disease", 59 Klin. Med.-(Mosk) 48-50 (1981).

Z. T. Zheng, et al., "Treatment of Gastrointestinal Ulcer by Furazolidone", 2 *Chinese J. of Digestion* 131-133 (1982).

L. Lu, et al., "Effect of Furaxon and It Analogs on Gastrointestinal Propulsion in Mice", 15 Beijing Yixueyuan Xuebao 185-187 (1983).

B. E. He, et al., "Cytoprotection of Furazolidone in Resistant-Soakage Gastric Ulcers in Rats", 4 Jinau Liyi Xuebao 55-59 (1984).

S. Zhang. et al., "Protective Effects of Furazolidone and Some Commonly Used Antiulcer Drugs on Several Gastric Ulcer Models in Rats", 19 Yaoxue Xuebao 5-11 (1984).

Physicians Desk Reference for Nonprescription Drugs 646 (1985).

B. J. Marshall, "Perspective-Campylobacter pyloridis and Gastritis" 153 *J. of Infectious Diseases* 650-657 (1986).

"Bismosal, Mixture Cholera Infantum, Norwich" (Advertisement) (1918).

"Stomach Upset" (Advertisement) (1951).

B. J. Marshall, I. Hislop et al, "Histological Improvement of Active Chronic Gastritis in Patients Treated with De-Nol", 14 Australia & New Zealand J. of Medicine 907 (Dec. 1984).

Antimicrobial Agents and Chemotherapy, Jul. 1980, pp. 118-121 Klin. Med. (Mosk) 59(2): 48-50 (Feb.) 1981 (translation).

Antimicrobial Agents and Chemotherapy, Apr. 1981, pp. 593-597.

Antimicrobial Agents and Chemotherapy, Oct. 1983, pp. 509-513.

Yaoxue Xuebao 19(1); 5-11, 1984 (translation).

Antimicrobial Agents and Chemotherapy, Dec. 1985, pp. 837-838; Aug. 1985, pp. 188-191.

The Journal of Infectious Diseases, vol. 153, No. 4 Apr. 1986, 650-657.

METHODS AND COMPOSITIONS FOR THE TREATMENT OF GASTROINTESTINAL DISORDERS

This is a continuation of application Ser. No. 062,271, filed Jun. 15, 1987, now abandoned, which is a continuation of application Ser. No. 744,841, filed on Jun. 13, 1985, now abandoned.

BACKGROUND OF THE INVENTION

This invention relates to methods and compositions for the treatment of gastrointestinal disorders in humans and other animals.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. (The upper gastrointestinal tract is generally defined as including the esophagus, the stomach, the duodenum, the jejunum, and ilium.) Gastritis is, by definition, typified by an inflammation of the stomach mucosa. In practice, though, the disorder is manifested by a broad range of poorly-defined, and heretofore inadequately treated, symptons such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, 1311–1315 (1984), and in R. Greenlaw, et al., "Gastroduodenitis, A Broader Concept of Peptic Ulcer Disease", 25 *Digestive Diseases and Sciences* 660–672 (1980).

Peptic ulcers are lesions of the gastrointestinal tract lining, characterized by loss of tissue due to the action of digestive acids and pepsin. It has been generally held that peptic ulcers are caused either by gastric hypersecretion, or (more often) by decreased resistance of the gastric lining to digestive acids and pepsin. The medical literature is replete with methods for treating ulcers, including modification of the diet, surgical removal of the lesions, and the use of drugs. Such drugs include: antacids, which serve to counteract excess gastric secretions; anticholinergics, which reduce acid secretion; $H_2$ antagonists, which also block the release of gastric acids; prostaglandins, which increase the resistance of the gastric lining to digestive fluids, and may also inhibit acid secretion; prokinetic agents, which enhance gastrointestinal tract motility; and compositions which form protective barriers over gastric lesions. Prescription and non-prescription drug therapies are generally described in Garnet, "Antacid Products", *Handbook of Non-prescription Drugs*, Chapter 3 (7th edition, 1982). One group of drugs which are thought to be effective due to coating of ulcer sites and forming protective barriers is the bismuth-containing drugs. See, for example, Koo, et al., "Selective Coating of Gastric Ulcers by Tripotassium Dicitrato Bismuthate in the Rat", 82 *Gastroenterology* 864–870 (1982).

Regardless of the particular drug composition used in treating gastrointestinal disorders, such as peptic ulcer disease, the treatment is often imprecise and incomplete. Actual "cures", i.e., successful treatment resulting in total remission of disease, are very often not effected. See, A. J. McLean, et al., "Cytoprotective Agents and Ulcer Relapse", 142 *The Medical Journal of Australia*, Special Supplement S25-S28 (1985). Furthermore, many conventional treatments may render subjects hypochlorhydric (i.e., with low levels of hydrochloric acid in the stomach) which may predispose them to other disorders, e.g., gastrointestinal infections, halitosis, and gastric carcinomas.

It has now been discovered that certain methods of treatment, involving the administration of bismuth and the administration of antimicrobials, are effective for the treatment of gastrointestinal disorders. In particular, as compared to treatment regimens known in the art, these methods cure, or afford lower relapse rates of, gastritis and peptic ulcer disease. These methods also afford other benefits in the treatment and management of subjects having gastrointestinal diseases, such as in not rendering treated subjects hypochlorhydric.

SUMMARY OF THE INVENTION

The present composition provides methods, for the treatment of a human or lower animal subject having a gastrointestinal disorder, comprising administering to said subject from about 50 milligrams to about 5000 milligrams of bismuth, per day, for from 3 to 56 days, and administering to said subject a safe and effective amount of an antimicrobial, per day, for from 1 to 21 days.

Typically, the antimicrobial is administered at a level of from about 100 milligrams to about 10,000 milligrams, per day. Preferably the bismuth is administered for from 1 to 21 days prior to initial administration of the antibiotic. Preferred methods of the present invention comprise administration of bismuth and administration of antimicrobials to human or lower animal subjects that have been tested for the presence of infection by pyloric campylobacter or other pathogenic organisms in the upper gastrointestinal tract, with positive results. A preferred test for such infection is through the detection of urease enzyme in the stomach.

This invention also provides compositions for the treatment of gastrointestinal disorders, comprising a safe and effective amount of bismuth and a safe and effective amount of an antimicrobial. These compositions are particularly useful in the processes of the present invention.

DESCRIPTION OF INVENTION

The methods of the present invention comprise treatment of humans or lower animals, having gastrointestinal disease, by administering bismuth and antimicrobials. Specific compounds and compositions to be used in the processes and compositions of the present invention must, accordingly, be pharmaceutically-acceptable. As used herein, such a "pharmaceutically-acceptable" component is one which is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse effects (such as toxicity, irritation, or allergic response) commensurate with a reasonable benefit/risk ratio when used in the manner of this invention. The specific "safe and effective amount" will, obviously, vary with such factors as the particular condition that is being treated, the severity of the condition, the duration of the treatment, the physical condition of the patient, the nature of concurrent therapy (if any), and the specific formulations employed in the present invention.

Specifically, the processes of the present invention, for the treatment of a human or lower animal subject having a gastrointestinal disorder, comprise administering to said subject from about 50 milligrams to about 5000 milligrams of bismuth, per day, for from 3 to 56 days, and administering to said subject a safe and effective amount of an antimicrobial, per day, for from 1 to 21 days.

As used herein, "gastrointestinal disorder" encompasses any disease or other disorder of the upper gastrointestinal tract of a human or lower animal. Such gastrointestinal disorders include, for example: disorders not manifested by presence of ulcerations in the gastric mucosa (herein "non-ulcerative gastrointestinal disorder"), including chronic or atrophic gastritis, non-ulcer dyspepsia, esophogeal reflux disease and gastric motility disorders; and "peptic ulcer disease", i.e., gastric, duodenal and jejunal ulcers. In particular, "gastrointestinal disorder" refers to such disorders of the upper gastrointestinal tract caused or mediated by bacteria, including campylobacter-like organisms (herein "CLO"), e.g., *Campylobacter pyloridis*. Such CLO include those described in J. R. Warren and B. J. Marshall, "Unidentified Curved Bacilli on Gastric Epithelium in Active Chronic Gastritis", *The Lancet* 1273-1275 (1983), incorporated by reference herein, and G. Kasper and N. Dickgiesser, "Isolation from Gastric Epithelium of Campylobacter-like Bacteria that are Distinct from 'Campylobacter Pyloridis'", *The Lancet* 111-112 (1985).

The processes of this invention encompass processes wherein the administering of bismuth and the administering of an antimicrobial are performed simultaneously (beginning and ending on the same day), concurrently (overlapping), or consecutively (sequential, but wherein the course of treatment is substantially continuous). Preferably, though, the step of administering the antimicrobial is not commenced prior to commencing the step of administering the bismuth.

As used herein, "administering" refers to any method which, in sound medical practice, delivers the compounds or compositions used in this invention to the subject to be treated in such a manner so as to be effective in the treatment of the gastrointestinal disorder. Preferably, then, the bismuth is administered orally. Also preferably, the antimicrobials are administered either orally, intravenously, or any other method which effects systemic distribution, or local distribution to the site of the CLO infection, of the antibiotic in the subject. Oral ingestion of the antibiotic is a preferred method of administering the antibiotic in the processes of this invention.

Bismuth:

The processes of this invention involve administration of from about 50 milligrams to about 5000 milligrams of bismuth, per day, for from 3 to 56 days. (As used herein, the quantity of bismuth is by weight of elemental bismuth. Thus, the actual weight of a bismuth-containing compound will be greater.) Preferably, from about 500 milligrams to about 1500 milligrams of bismuth are administered, per day. The preferred duration of bismuth administration will vary according to the specific gastrointestinal disorder to be treated. In general, though, in methods for treatment of non-ulcerative gastrointestinal disorders, the bismuth is administered for from 3 to 21 days. The bismuth is preferably adminstered, in methods for treatment of peptic ulcer disease, for from 14 to 56 days.

In the processes of this invention, the bismuth is preferably administered as a pharmaceutically-acceptable salt. Such bismuth salts include, for example, bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. The bismuth useful herein may be administered alone, or in combination with other pharmaceutically-acceptable components, in a bismuth-containing composition. A variety of such compositions containing bismuth salts are commercially-available, including, for example, DeNol, containing tripotassium dicitrato bismuthate (sold by Gist-Brocades N.V.), Noralac, containing bismuth aluminate, alginic acid, and magnesium carbonate (manufactured by North American Pharmaceuticals), Roter bismuth, containing bismuth subnitrate (sold by Roter Laboratories), Fensobar Polvo, containing bismuth subcarbonate among other materials (manufactured by USV Pharmaceutical Corporation), and Pepto-Bismol, containing bismuth subsalicylate (sold by The Procter & Gamble Company).

Antimicrobial:

The processes of the present invention also include administration of a safe and effective amount of an antimicrobial, per day, for from 1 to 21 days. Typically, the antimicrobial is administered at a level of from about 100 milligrams to about 10,000 milligrams, per day. Preferably, the antimicrobial is administered for from 1 day to 14 days. The specific dosage of antimicrobial to be administered, as well as the duration of antimicrobial treatment, are mutually dependent, and will also depend upon such factors as the specific antimicrobial used, the resistance pattern of the infecting organism to the antimicrobial used, the ability of the antimicrobial to reach minimum inhibitory concentrations at the site of the infection, the nature and extent of other infections (if any), the personal attributes of the subject, compliance with the treatment regimen, and the presence and severity of any side effects of the treatment.

A wide variety of antimicrobials are useful in this invention. As used herein, such "antimicrobials" refer to any naturally-occurring, synthetic or semi-synthetic compound or composition, or mixture thereof, which is safe for human use as used in the processes of this invention, and is effective in killing or substantially inhibiting the growth of CLO when used in the processes of this invention. Antibiotics are among the preferred antimicrobials useful herein. Such antibiotics can be generally classified by chemical composition, into the following principal groups: the aminoglycosides, such as gentamicin, neomycin, kanamycin, and streptomycin; the macrolides, such as erythromycin, clindamycin, and rifampin; the penicillins, such as penicillin G, penicillin V, ampicillin and amoxycillin; the polypeptides, such as bacitracin and polymyxin; the tetracyclines, such as tetracycline, chlortetracycline, oxytetracycline, and doxycycline; the cephalosporins, such as cephalexin and cephalothin; and such miscellaneous antibiotics as chloramphenicol and clindamycin. These antibiotics can be generally said to function in one of four ways: inhibition of cell walls synthesis, alteration of cell wall permeability, inhibition of protein synthesis, or inhibition of nucleic acid synthesis.

Other antimicrobials useful herein include the sulfonamides; nitrofurans, such as nitrofurazone nitrofurantion, and furozolidone; and metronidazole, tinidazole, and nimorazole. Antimicrobials among those useful herein are described in the following publications, incorporated by reference herein: *Remington's Pharmaceutical Sciences* (15th edition 1975); F. H. Meyers, et al., *Review of Medical Pharmacology* (7th edition 1980); *Gaddum's Pharmocology* (8th edition 1978); and A. Goodman, A. G. Goodman and L. S. Gilman, *The Pharmacological Basis of Therapeutics* (6th edition 1980).

While any of these antimicrobials may be used, penicillin, erythromycin, doxycycline, metronidazole, tinidazole, amoxycillin, ampicillin, and nitrofurantoin are among the preferred antimicrobials for use in the present invention. In a preferred method of treatment, a sample of CLO is obtained from the stomach of the subject to be treated, as by biopsy, aspiration, or by other suitable method, and the organism cultured and tested for sensitivity to the various antimicrobials useful herein. Preferably such sensitivity testing is by determination of the relative minimum inhibitory concentrations of the antimicrobials using broth or plate dilution techniques. The antimicrobial found to be most effective against the cultured bacteria (i.e., effective at the lowest minimum inhibitory concentration) is then selected for use in the methods of this invention.

As stated above, the specific preferred quantity of antimicrobial, and duration of treatment used in the methods of this invention will, in addition to other factors, depend upon the particular antimicrobial used and its pharmacology. In general, though, the tetracyclines are preferably administered at a level of from about 100 milligrams to about 2000 milligrams, per day. Macrolides (such as erythromycin) are preferably administered at a level of from about 1000 milligrams to about 4000 milligrams, per day. Penicillins are preferably administered at a level of from about 500 milligrams to about 3000 milligrams, per day. The aminoglycosides (such as neomycin) are, preferably, administered at a level of from about 100 milligrams to about 8000 milligrams, per day. Nitrofurans (such as nitrofurantoin) are administered preferably at levels of from about 100 milligrams to about 800 milligrams, per day. Preferably, metronidazole is administered at a level of from about 500 to about 2000 milligrams, per day.

The specific method of administering the antimicrobial, according to the processes of this invention, may depend upon such factors as the particular antimicrobial used, the site of infection, the amount of antimicrobial to be administered per day, the presence of any adverse side effects, and the interactions (if any) between the antimicrobial and the bismuth. Thus, the antimicrobials may be administered under the process of this invention by single daily doses, or by administration in two three, four, or more doses per day. One factor, in particular, is potential interaction between the antimicrobial and the bismuth administered under these processes. For example, the presence of bismuth is known to adversely affect the efficacy of the tetracyclines. See, for example, C. D. Ericsson, et. al., "Influence of Subsalicylate Bismuth on Absorption of Doxycycline" 247 *J. of American Medical Assoc.* 2266 (1982). Hence, it is preferred to adminster those antimicrobials that are subject to adverse bismuth interaction by methods that minimize such interactions, i.e., by minimizing the simultaneous presence of antimicrobial and bismuth in the stomach. Such methods include one or more of the following: staggered oral dosing of the bismuth and antimicrobial, through discrete administration of each compound or composition separated by at least (preferably) two hours between dosages; oral administration of the antimicrobial in an enterically coated form, i.e., coating of the antimicrobial which prevents dissolution of the antimicrobial in the stomach; use of optional processes of this invention, wherein the step of administering bismuth is terminated prior to commencing the step of orally administering the antimicrobial; and administering the antimicrobial by a non-oral route, e.g., by intraveneous or intramuscular injection.

Bismuth/Antimicrobial Compositions:

The present invention also provides compositions, for the treatment of gastrointestinal disorders, comprising a safe and effective amount of bismuth and a safe and effective amount of an antimicrobial. Typically, these compositions comprise:

(a) from about 50 milligrams to about 5000 milligrams of bismuth; and (b) from about 100 milligrams to about 10,000 milligrams of an antimicrobial.

Preferably, the bismuth salt is present at a level of from about 250 milligrams to about 1000 milligrams. Also preferably, the antimicrobial is present at a level of from about 100 milligrams to about 1000 milligrams.

The compositions of the present invention may contain optional components which affect the physical and therapeutic characteristics of the present compositions. In particular, a variety of pharmaceutically-acceptable carriers and excipients may be included, depending upon the particular dosage form to be used. Various oral dosage forms can be used, including such solid forms as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweetners, melting agents, coloring, and flavoring agents.

Specific examples of pharmaceutically-acceptable carriers and excipients that may be used to formulate oral dosage forms of the present invention are described in U.S. Pat. No. 3,903,297, Robert, issued Sept. 2, 1975, incorporated by reference herein. Techniques and compositions for making dosage forms useful herein are described in the following references, all incorporated by reference herein: 7 *Modern Pharmaceutics*, Chapters 9 and 10 (Banker and Rhodes, editors, 1979); an Lieberman, et al., *Pharmaceutical Dosage Forms: Tablets* (1981); and Ansel, *Introduction to Pharmaceutical Dosage Forms* (2d edition, 1976).

As discussed above, care must be taken in avoiding any interactions between the bismuth compound or composition and the particular antimicrobial used in these compositions. Accordingly, in preferred compositions of this invention, the antimicrobial is physically separated from the bismuth, in such a manner so that the antimicrobial and the bismuth are not simultaneously dissolved in the stomach. Hence, a preferred composition of this invention comprises a capsule containing bismuth particles and enterically-coated antimicrobial particles.

The compositions of this invention may be used according to the methods of this invention, by administering the composition from 1 to 7 times, per day, for from 3 to 21 days. The specific frequency of administration will depend upon such factors as the specific bismuth compound or composition and antimicrobial used, the levels at which the components are incorporated in the composition, the nature and severity of the condition to be treated, and the nature of any concurrent therapy (if any).

Optional Components and Methods:

The methods of this invention may incorporate optional steps modifying the methods of treatment of this invention. Such optional steps may also utilize optional components or compositions. Such optional components or compositions must not, however, adversely affect the therapeutic activity of the bismuth or of the antimicrobial used in the present methods.

A preferred optional method of the present invention involves a delay, preferably of from 1 to 21 days, more preferably from 1 to 10 days, more preferably from 1 to 5 days, in the administration of antimicrobial after initial administration of a bismuth salt. Such preferred methods for the treatment of a human or lower animal subject having a gastrointestinal disorder thus comprise the steps of:

a) administering to said subject from about 50 to about 5000 milligrams of a bismuth salt, per day, for from 3 to 56 days; and b) administering to said subject a safe and effective amount of an antimicrobial, per day, for from about 1 to about 21 days;

wherein said step of administering an antimicrobial is commenced from 1 to 21 days after the commencement of said step of administering bismuth. Also preferably, a sample of gastric material is obtained from the stomach of the subject, and the infecting CLO cultured and tested for sensitivity to the antimicrobials useful herein (as described above) during the period of initial administration of bismuth but prior to administration of antimicrobial.

Another preferred method of this invention includes a step for the detection of CLO in the upper gastrointestinal tract of the human or lower animal subject. The methods for detection useful in such preferred steps of this invention include gram stains of gastric tissues (obtained, for example, by biopsy), serologic tests to detect the presence of antibodies to the organisms, tests of body fluids to detect the presence of metabolites of the organisms, silver or other specially stained tissue sections of tissues, and detection of urease enzyme in the stomach of the subject. Such detection steps are also described in copending application Ser. No. 744,842, Marshall, "Methods for the Treatment of Gastrointestinal Disorders", filed Jun. 13, 1985 (incorporated by reference herein).

One preferred method of detection, useful in a preferred process of this invention, is the detection of urease enzyme (urea amidohydrolase) in the stomach of the human or lower animal having a gastrointestinal disorder. Such a detection step may include, for example, obtaining a sample of gastric fluid (e.g., from a gastric tube or vomitus) or of gastric mucosa (e.g., by biopsy) and analyzing the material for the presence of urease enzyme. One such method for the diagnosis of gastrointestinal disorder is described in copending application Ser. No. 744,840, Marshall, "Compositions and Methods For The Diagnosis of Gastrointestinal Disorders", filed Jun. 13, 1985. Such methods involve obtaining a sample of gastric mucosa and placing said sample into a composition which comprises:

a) urea, at a concentration of from about 10 to about 40 grams per liter;

b) a bactericide, at a concentration of from about 1 to about 5 grams per liter;

c) an indicator having a $pK_a$ of from about 6.5 to about 8.5, at an effective concentration; and d) water;

wherein said composition has a pH of from about 5.0 to about 6.5 and said pH is at least one pH unit lower than the $pK_a$ of said indicator. Preferably, the composition contains a gelling agent, such as a non-nutritive agar, at a concentration of from about 5 to about 50 grams per liter. Typically, the indicator is present at a concentration of from about 20 to about 100 milligrams per liter. (As used herein, all concentrations are by weight of component per total volume of composition.) A change in the color of the composition indicates the presence of urease enzyme, and the presence of a gastrointestinal disorder.

The diagnostic step is preferably performed prior to the step of administering bismuth. Also preferably, the diagnostic step is repeated during the step of administering bismuth, and the step of administering bismuth is terminated after the diagnostic step yields a negative result. Thus, a preferred method of the present invention, for the treatment of a human or lower animal subject having a gastrointestinal disorder, comprises the steps of:

a) performing a diagnostic test on said subject for the detection of a CLO infection of said subject; and, upon obtaining a positive result from said diagnostic test, b) administering to said subject from about 50 milligrams to about 5000 milligrams of bismuth, per day, for a period of time ending when said subject is tested with said diagnostic test and a negative result is obtained; followed by c) administering from about 100 milligrams to about 10000 milligrams of an antimicrobial, per day, for from 1 to 21 days.

The following non-limiting examples illustrate the compositions, processes, and uses of the present invention.

EXAMPLE I

A human subject, suffering from atrophic gastritis, was treated by a method of the present invention. Specifically, the subject was endoscoped and a biopsy was taken of the gastric mucosa of the subject. Analysis of the biopsy sample showed inflammation of the mucosa, and depletion of the protective mucous layer. The subject was then treated, according to the present invention, by administering a composition containing tripotassium dicitrato bismuthate, manufactured by Gist-Brocades, N. V. and sold under the name "DeNol". The composition, in tablet form (each tablet containing 120 milligrams of bismuth) was administered four times daily (for a total of 480 milligrams of bismuth administered per day) for 28 days. Amoxicillin tablets (each tablet contained 500 milligrams) was concurrently administered three times daily (for a total of 1500 milligrams antibiotic per day) for 21 days. The subject was endoscoped and biopsied again 28 days after treatment began, finding essentially normal, healed gastric mucosa. The subject remained asymptomatic, and another biopsy performed five months later also revealed normal gastric mucosa.

In the above example, bismuth citrate, bismuth tartrate, bismuth subcitrate and bismuth subsalicylate are substituted, respectively, for tripotassium dicitrato bismuthate, with substantially-similar results. Similarly, penicillin, doxycycline, erythromycin and ampicillin are substituted, respectively, for amoxycillin, with substantially-similar results.

EXAMPLE II

A composition, according to the present invention, is made comprising:

| | |
|---|---|
| bismuth subsalicylate | 0.5 g |
| penicillin | 0.5 g |
| magnesium stearate | 0.4 g |

The composition is made by simple admixture of the components and pressed into tablets using conventional methods. The composition is then administered, according to the methods of this invention, to a human subject having peptic ulcer disease, three times daily for fourteen days. The subject, after treatment, is endoscoped, revealing healing of the peptic ulcer lesion, and histologic absence of active chronic gastritis and of CLO.

EXAMPLE III

A human subject, suffering from peptic ulcer disease, is treated by a method of this invention. Specifically, a sample of vomitus is obtained from the individual and analyzed for the presence of urease. After detecting urease, the individual is then treated by administering 500 milligrams of bismuth subsalicylate, per day (two doses per day) for 28 days. After the fifth day (commencing on the sixth day) of bismuth treatment, the subject is also treated by administering 750 milligrams of nitrofurantoin, per day, for 14 days. (Hence, the bismuth treatment continues for 9 days after the last day of antimicrobial treatment.) The subject is then endoscoped, revealing healing of the peptic ulcer lesion.

In the above example, nitrofurazone, metronidazole, and tinidazole are substituted, respectively, for nitrofurantoin, with substantially-similar results.

EXAMPLE IV

A human subject, suffering from non-ulcer dyspepsia, is treated by a method of this invention. Specifically, a biopsy of gastric mucosa is taken from the stomach of the subject. The sample is then placed in 0.5 milliliters of an aqueous gel of a composition having the following composition:

| Component | Quantity grams | Final Concentration |
|---|---|---|
| urea | 3.000 | 30 g/l |
| phenol red* | 0.008 | 80 mg/l |
| methyl hydroxy benzoate | 0.200 | 2 g/l |
| bacteriological agar | 1.500 | 15 g/l |
| citric acid | 0.040 | 400 mg/l |
| sodium phosphate | 0.080 | 800 mg/l |

*phenol sulfonphthalein indicator, having $pK_a = 7.9$, exhibiting a yellow color in undissociated state (below pH 6.4) and red color in dissociated state (above pH 8.2)

(The components, except urea, are dissolved in 100 milliliters of water, heated to approximately 65° C., and stirred until the solution is clear. The composition is allowed to cool to below approximately 45° C. and the urea is added. Upon cooling to ambient temperature, a gel is formed having a pH of 6.0 and a deep yellow color.) After the biopsy sample is inserted into the composition, the composition color changes from yellow to red over a period of approximately fifteen minutes, indicating the presence of urea in the biopsy sample and presence of CLO in the stomach of the subject. The subject is then treated by administering 500 milligrams of bismuth, as bismuth subsalicylate, per day, for 10 days. On the tenth day of bismuth treatment, the subject is also administered 5000 milligrams of penicillin, by intraveneous injection. Five days later the subject is endoscoped, revealing normal gastric mucosa, and a biopsy sample obtained. The sample is then inserted into 0.5 milliliters of a test composition comprised as above, and the color of the composition remained unchanged after 24 hours, indicating lack of CLO infection.

What is claimed is:

1. A method, for the treatment of a human or lower animal subject having an infectious upper gastrointestinal tract disorder caused or mediated by a Campylobacter pyloridis infection in said subject, comprising administering to said subject a pharmaceutically-acceptable bismuth agent and a pharmaceutically-acceptable antimicrobial agent in amounts safe and effective for combatting the Campylobacter pyloridis infection.

2. A method, according to claim 1, for the treatment of a human or lower animal subject having an infectious upper gastrointestinal tract disorder caused or mediated by Campylobacter pyloridis, comprising administering to said subject from about 50 milligrams to about 5000 milligrams of bismuth, per day, for from 3 to 56 days, and administering to said subject a safe and effective amount of an antimicrobial, per day, for from 1 to 21 days.

3. A method, according to claim 1, wherein said antimicrobial is administered at a level of from about 100 milligrams to about 10,000 milligrams, per day.

4. A method, according to claim 2, wherein said bismuth is administered at a level of from about 500 milligrams to about 1500 milligrams, per day.

5. A method, according to claim 2, for the treatment of a human or lower animal subject having an infectious non-ulcerative upper gastrointestinal tract disorder caused or mediated by Campylobacter pyloridis, wherein said bismuth is administered for from 3 to 21 days.

6. A method, according to claim 2, for the treatment of a human or lower animal subject having an infectious peptic ulcer disease caused or mediated by Campylobacter pyloridis, wherein said bismuth is administered for from 14 to 56 days.

7. A method, according to claim 2, wherein said antimicrobial is administered for from 1 to 14 days.

8. A method, according to claim 3, wherein said antimicrobial is an antibiotic.

9. A method, according to claim 4, wherein said bismuth is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof.

10. A method, according to claim 9, wherein said bismuth is tripotassium dicitrato bismuthate.

11. A method, according to claim 9, wherein said bismuth is bismuth subsalicylate.

12. A method, according to claim 2, wherein said step of administering an antimicrobial is commenced from 1 to 21 days after the commencement of said step of administering bismuth.

13. A method, according to claim 2, comprising the steps of administering said bismuth; followed by administering said antimicrobial.

14. A method, for the treatment of a human or lower animal subject having an infectious upper gastrointestinal tract disorder caused or mediated by Campylobacter pyloridis, comprising the steps of:
 (a) performing a diagnostic test on said subject for the detection of a Campylobacter pyloridis infection of said subject; and upon obtaining a positive result from said diagnostic test,
 (b) combatting said Campylobacter pyloridis infection in said subject by administering to said subject a composition comprising a pharmaceutically-acceptable bismuth agent and a composition comprising a pharmaceutically-acceptable antimicrobial agent in amounts to clear said subject of symptoms of said infection.

15. A method, according to claim 14, wherein said bismuth is administered for a period of time ending when said subject is tested with said diagnostic test and a negative result is obtained.

16. A method, for the treatment of a human or lower animal subject having an infectious upper gastrointestinal tract disorder caused or mediated by a Campylobacter pyloridis infection in said subject, comprising administering to said subject a pharmaceutically-acceptable bismuth salt and a pharmaceutically-acceptable antimicrobial agent in amounts safe and effective for combating the Campylobacter pyloridis infection.

17. A method according to claim 16 wherein said pharmaceutically-acceptable bismuth salt is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof.

18. A method according to claim 17 wherein said pharmaceutically-acceptable salt is tripotassium dicitrato bismuthate.

19. A method according to claim 18 wherein said antimicrobial is an antibiotic.

20. A method according to claim 18 wherein said antimicrobial is selected from the group consisting of gentamicin, neomycin, kanamycin, streptomycin, erythromycin, rifampin, penicillin G, penicillin V, ampicillin, amoxycillin, bacitracin, polymyxin, tetracycline, chlortetracycline, oxytetracycline, doxycyline, cephalexin, cephalothin, chloramphenicol, clindamycin, sulfonamides, nitrofurazone, nitrofurantoin, furozolidone, metronidazole, tinidazole, nimorazole, and mixtures thereof.

21. A method according to claim 18 wherein said antimicrobial is selected from amoxicillin, tinidazole, metronidazole, and mixtures thereof.

22. A method according to claim 18 wherein said antimicrobial is metronidazole.

23. A method according to claim 17 wherein said pharmaceutically-acceptable bismuth salt is bismuth subsalicylate.

24. A method according to claim 23 wherein said antimicrobial is an antibiotic.

25. A method according to claim 23 wherein said antimicrobial is selected from the group consisting of gentamicin, neomycin, kanamycin, streptomycin, erythromycin, rifampin, penicillin G, penicillin V, ampicillin, amoxycillin, bacitracin, polymyxin, tetracycline, chlortetracycline, oxytetracycline, doxycyline, cephalexin, cephalothin, chloramphenicol, clindamycin, sulfonamides, nitrofurazone, nitrofurantoin, furozolidone, metronidazole, tinidazole, nimorazole, and mixtures thereof.

26. A method according to claim 25 wherein said antimicrobial is selected from amoxicillin, tinidazole, metronidazole, and mixtures thereof.

27. A method according to claim 26 wherein said antimicrobial is metronidazole.

28. A method, for the treatment of a human or lower animal subject having an infectious non-ulcerative upper gastrointestinal tract disorder caused or mediated by Campylobacter pyloridis, comprising administering to said subject:
 (a) a safe and effective amount for treating said Campylobacter pyloridis infection of a pharmaceutically-acceptable bismuth salt, wherein said bismuth salt is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate and mixtures thereof; and
 (b) a safe and effective amount for treating said Campylobacter pyloridis infection of a pharmaceutically-acceptable antimicrobial agent, wherein said antimicrobial agent is selected from the group consisting of gentamicin, neomycin, kanamycin, streptomycin, erythromycin, rifampin, penicillin G, penicillin V, ampicillin, amoxycillin, bacitracin, polymyxin, tetracycline, chlortetracycline, oxytetracycline, doxycyline, cephalexin, cephalothin, chloramphenicol, clindamycin, sulfonamides, nitrofurazone, nitrofurantoin, furozolidone, metronidazole, tinidazole, nimorazole, and mixtures thereof.

29. A method according to claim 28 wherein said bismuth salt is selected from bismuth subsalicylate, tripotassium dicitrato bismuthate, and mixtures thereof, and said antimicrobial agent is selected from amoxicillin, tinidazole, metronidazole, and mixtures thereof.

30. A method, for the treatment of a human or lower animal subject having infectious gastritis caused or mediated by Campylobacter pyloridis infection, comprising administering to said subject:
 (a) a safe and effective amount for treating said Campylobacter pyloridis infection of a pharmaceutically-acceptable bismuth salt, wherein said bismuth salt is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate and mixtures thereof; and (b) a safe and effective amount for treating said Campylobacter pyloridis infection of a pharmaceutically-acceptable antimicrobial agent, wherein said antimicrobial agent is selected from the group consisting of gentamicin, neomycin, kanamycin, streptomycin, erythromycin, rifampin, penicillin G, penicillin V, ampicillin, amoxycillin, bacitracin, polymyxin, tetracycline, chlortetracycline, oxytetracycline, doxycyline, cephalexin, cephalothin, chloramphenicol, clindamycin, sulfonamides, nitrofurazone, nitrofurantoin, furozolidone, metronidazole, tinidazole, nimorazole, and mixtures thereof.

31. A method according to claim 30 wherein said bismuth salt is selected from bismuth subsalicylate, tripotassium dicitrato bismuthate, and mixtures thereof, and said antimicrobial agent is selected from amoxicillin, tinidazole, metronidazole, and mixtures thereof.

32. A method according to claim 31 comprising administering to said subject bismuth subsalicylate and metronidazole.

33. A method according to claim 31 comprising administering to said subject tripotassium dicitrato bismuthate and metronidazole.

34. A method, for the treatment of a human or lower animal subject having infectious non-ulcerative dyspepsia caused or mediated by Campylobacter pyloridis, comprising administering to said subject:

(a) a safe and effective amount for treating said Campylobacter pyloridis infection of a pharmaceutically-acceptable bismuth salt, wherein said bismuth salt is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate and mixtures thereof; and (b) a safe and effective amount for treating said Campylobacter pyloridis infection of a pharmaceutically-acceptable antimicrobial agent, wherein said antimicrobial agent is selected from the group consisting of gentamicin, neomycin, kanamycin, streptomycin, erythromycin, rifampin, penicillin G, penicillin V, ampicillin, amoxycillin, bacitracin, polymyxin, tetracycline, chlortetracycline, oxytetracycline, doxycyline, cephalexin, cephalothin, chloramphenicol, clindamycin, sulfonamides, nitrofurazone, nitrofurantoin, furozolidone, metronidazole, tinidazole, nimorazole, and mixtures thereof.

35. A method according to claim 34 wherein said bismuth salt is selected from bismuth subsalicylate, tripotassium dicitrato bismuthate, and mixtures thereof, and said antimicrobial agent is selected from amoxicillin, tinidazole, metronidazole, and mixtures thereof.

36. A method according to claim 35 comprising administering to said subject bismuth subsalicylate and metronidazole.

37. A method according to claim 35 comprising administering to said subject tripotassium dicitrato bismuthate and metronidazole.

38. A method, for the treatment of a human or lower animal subject having an infectious peptic ulcer disease caused or mediated by Campylobacter pyloridis, comprising administering to said subject:

(a) a safe and effective amount for treating said Campylobacter pyloridis infection of a pharmaceutically-acceptable bismuth salt, wherein said bismuth salt is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate and mixtures thereof; and (b) a safe and effective amount for treating said Campylobacter pyloridis infection of a pharmaceutically-acceptable antimicrobial agent, wherein said antimicrobial agent is selected from the group consisting of gentamicin, neomycin, kanamycin, streptomycin, erythromycin, rifampin, penicillin G, penicillin V, ampicillin, amoxycillin, bacitracin, polymyxin, tetracycline, chlortetracycline, oxytetracycline, doxycyline, cephalexin, cephalothin, chloramphenicol, clindamycin, sulfonamides, nitrofurazone, nitrofurantoin, furozolidone, metronidazole, tinidazole, nimorazole, and mixtures thereof.

39. A method according to claim 38 wherein said bismuth salt is selected from bismuth subsalicylate, tripotassium dicitrato bismuthate, and mixtures thereof, and said antimicrobial is selected from amoxicillin, tinidazole, metronidazole, and mixtures thereof.

40. A method according to claim 38, for the treatment of a human or lower animal subject having a duodenal ulcer, comprising administering to said subject bismuth subsalicylate and metronidazole.

41. A method according to claim 38, for the treatment of a human or lower animal subject having a duodenal ulcer, comprising administering to said subject tripotassium dicitrato bismuthate and metronidazole.

42. A method according to claim 38, for the treatment of a human or lower animal subject having a gastric ulcer, comprising administering to said subject bismuth subsalicylate and metronidazole.

43. A method according to claim 38, for the treatment of a human or lower animal subject having a gastric ulcer, comprising administering to said subject tripotassium dicitrato bismuthate and metronidazole.

44. A method for the treatment of a human or lower animal subject having an infectious non-ulcerative upper gastrointestinal tract disorder caused or mediated by Campylobacter pyloridis, by combatting said Campylobacter pyloridis infection in said subject comprising the step of administering to said subject a composition comprising a pharmaceutically-acceptable bismuth agent and a composition comprising a pharmaceutically-acceptable antimicrobial agent in amounts to clear said subject of symptoms of said infection.

45. A method for the treatment of a human or lower animal subject having infectious gastritis caused or mediated by Campylobacter pyloridis, by combatting said Campylobacter pyloridis infection in said subject comprising the step of administering to said subject a composition comprising a pharmaceutically-acceptable bismuth agent and a composition comprising a pharmaceutically-acceptable antimicrobial agent in amounts to clear said subject of symptoms of said infection.

46. A method for the treatment of a human or lower animal subject having infectious non-ulcerative dyspepsia caused or mediated by Campylobacter pyloridis, by combatting said Campylobacter pyloridis infection in said subject comprising the step of administering to said subject a composition comprising a pharmaceutically-acceptable bismuth agent and a composition comprising a pharmaceutically-acceptable antimicrobial agent in amounts to clear said subject of symptoms of said infection.

47. A method for the treatment of a human or lower animal subject having infectious peptic ulcer disease caused or mediated by Campylobacter pyloridis, by combatting said Campylobacter pyloridis infection in said subject comprising the step of administering to said subject a composition comprising a pharmaceutically-acceptable bismuth agent and a composition comprising a pharmaceutically-acceptable antimicrobial agent in amounts to clear said subject of symptoms of said infection.

48. A method for the treatment of a human or lower animal subject having infectious duodenal ulcers caused or mediated by Campylobacter pyloridis, by combatting said Campylobacter pyloridis infection in said subject comprising the step of administering to said subject a composition comprising a pharmaceutically-acceptable bismuth agent and a composition comprising a pharmaceutically-acceptable antimicrobial agent in amounts to clear said subject of symptoms of said infection.

49. A method for the treatment of a human or lower animal subject having infectious gastric ulcers caused or mediated by Campylobacter pyloridis, by combatting said Campylobacter pyloridis infection in said subject comprising the step of administering to said subject a composition comprising a pharmaceutically-acceptable bismuth agent and a composition comprising a pharmaceutically-acceptable antimicrobial agent in amounts to clear said subject of symptoms of said infection.

* * * * *